United States Patent [19]

Bononi

[11] Patent Number: 4,963,013
[45] Date of Patent: Oct. 16, 1990

[54] PROTECTIVE SPECTACLES
[75] Inventor: Walter H. Bononi, Fellbach-Schmiden, Fed. Rep. of Germany
[73] Assignee: Marwitz & Hauser, Stuttgart, Fed. Rep. of Germany
[21] Appl. No.: 616,577
[22] Filed: Jun. 4, 1984
[30] Foreign Application Priority Data Jun. 4, 1983 [DE] Fed. Rep. of Germany ....... 3320351

[51] Int. Cl.$^5$ .............................................. G02C 5/16
[52] U.S. Cl. ..................................... 351/114; 351/111
[58] Field of Search ........................ 351/111, 113, 114; 2/449, 451

[56] References Cited

U.S. PATENT DOCUMENTS

| 2,012,759 | 8/1935 | Hefner | 351/114 |
| 3,052,160 | 9/1962 | Ratti | 351/114 |
| 3,436,761 | 4/1969 | Liautaud et al. | 351/44 |
| 4,298,991 | 11/1981 | Recenello | 2/451 |
| 4,547,909 | 10/1985 | Bell | 2/449 X |

FOREIGN PATENT DOCUMENTS

| 2062829 | 8/1973 | Fed. Rep. of Germany | 351/44 |
| 466782 | 11/1951 | Italy | 351/114 |
| 490050 | 8/1938 | United Kingdom | 351/114 |

OTHER PUBLICATIONS

Cutters Exchange, Safety Goggles,-1968.

Primary Examiner—Rodney B. Bovernick

[57] ABSTRACT

Protective spectacles have a protective shield, fitted in the temple region, to protect the eyes from dust, etc., coming from the side. According to West German Industrial Standards, DIN, a predetermined degree of sealing must be maintained, according to the purpose of use, between it and the spectacle frame. Protective shields attached rigidly to the frame are cumbersome. The protective shield is firmly connected by its upper edge region to the associated spectacle earpiece. It is thus pivoted away together with the earpiece. Its forward edge seals with the spectacle frame with a predetermined degree of sealing. So that this is not impaired by adjustment of the inclination, the earpiece has a bending zone behind the protective shield. The inclination is adjusted by bending the earpiece. The invention may be used for protective spectacles in the industrial and private fields.

4 Claims, 3 Drawing Sheets

PROTECTIVE SPECTACLES

BACKGROUND OF THE INVENTION

Statements concerning concepts in this field can be found in West German Industrial Standard No. DIN 58,210, 58,212. Such protective spectacles have different requirements for degree of sealing, according to the use for which they are intended. For example, they must be sealed against gases and fine dust, or else be sealed against coarse dust, or else sealed against dripping or spraying liquid.

OBJECT AND STATEMENT OF THE INVENTION

The object of the invention is to provide spectacles of the kind described, in which these degrees of sealing can be achieved as desired, and in fact when a protective shield is used.

According to the invention, this problem is solved by:

(a) Protective shields extend out rearward from the side profile sections of the frame in the opened state of the earpieces.

(b) The protective shields are firmly connected at their upper edge regions to an associated earpiece, and (c) A predetermined bending zone is located on each earpiece following the protective shield.

The inclination per se is adjusted by bending in the hinge region. The invention retains, however, the geometric relationships between the protective shield and the side profile section of the frame, so that the sealing properties do not change in this region. The inclination adjustment is effected in the bending zone, so that the protective spectacles can be adjusted according to the desired inclination, but on the other hand the sealing properties are not altered. Advantageously, the invention includes the following additional features.

The protective shield, at its forward edge, forms together with an opposite region of the side profile section, a sealed overlapping profile. This degree of sealing is achieved, according to this feature, by technically simple means, which can also be kept esthetic.

The protective shield is integral with the earpiece. This feature prevents the protective shield's being able to assume another position relative to the earpiece, which would, e.g., be the case if the protective shield were fastened to the earpiece e.g. with a dovetail joint.

The protective shield is of translucent material. The protective shield is given its blinkers action by this feature.

The protective shield is of transparent material. By this feature, vision in the edge region which is important in the physiology of vision is as if the protective shield were practically not present.

The overlapping profile is substantially linear in side view of the spectacles, and in front view follows a radius which is bent downwards and inwards from the hinge. This feature makes it possible to unite the requirements for the degree of sealing with the esthetic requirements. Apart from this, they facilitate production and mounting in parts of linear character. The geometry of the interengagement, or engagement over one another, respectively, of the parts of the overlapping profile then remains simple.

The frame has an upper back which provides a gripping lateral jaw and anchors the second hinge half; and the earpiece has a small plate above and to the side of the hinge pivot axis, which engages in a complementary recess of the frame above the lateral jaw. By this feature, the protection can, in an esthetic manner, be brought up even higher than the earpiece.

The bending zone directly adjoins the protective shield. The feature makes it possible for a relatively small amount of bending to give the inclination action.

The bending zone has horizontal weakening notches. By this feature, relatively little work is needed for the inclination, and apart from this the inclination bend is at the desired place.

The bending zone has vertical weakening notches. By this feature, the pressure with which the ends of the earpieces are to rest against the head can be adjusted with the same advantages.

The weakening notches run annularly around the earpiece. The feature leads to simple production and prevents breaking of the material of the ear yoke at the transition from one kind of notch to the other.

The earpiece has a metal wire inlay. By this feature, earpieces of the usual strength can be used, which nevertheless retain their stiffness. The metal wire inlay then takes over the essential part of those forces which are necessary for maintaining the set geometry.

DESCRIPTION OF THE DRAWINGS

The invention will now be described with reference to a preferred embodiment.

In the drawings there are shown.

DETAILED DESCRIPTION

Figure 1:
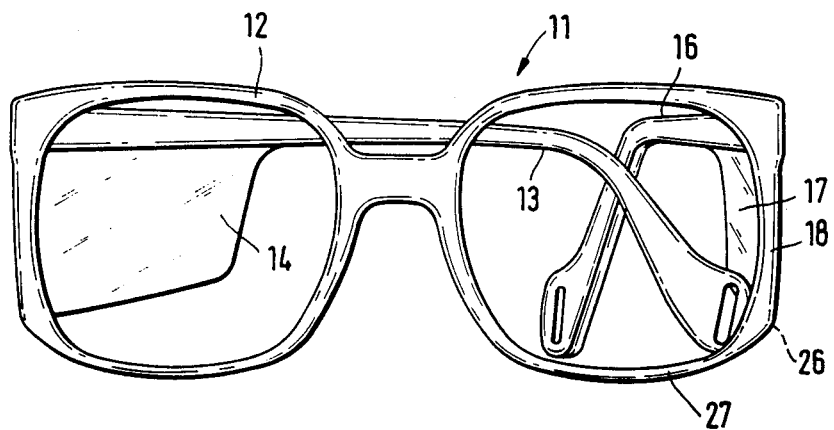
FIG. 1 The front view of the protective spectacles, with the right-hand earpiece folded in, FIG. 2 the side view of FIG. 1, FIG. 3 the inner view of the folded-back earpiece of FIG. 1 in the demonted state, FIG. 4 the rear view of the right-hand region of FIG. 1, FIG. 5 a perspective view of the side profile section in partially opened state of the earpiece, FIG. 6 a section along the line 6—6 in FIG. 2.
Figure 2:
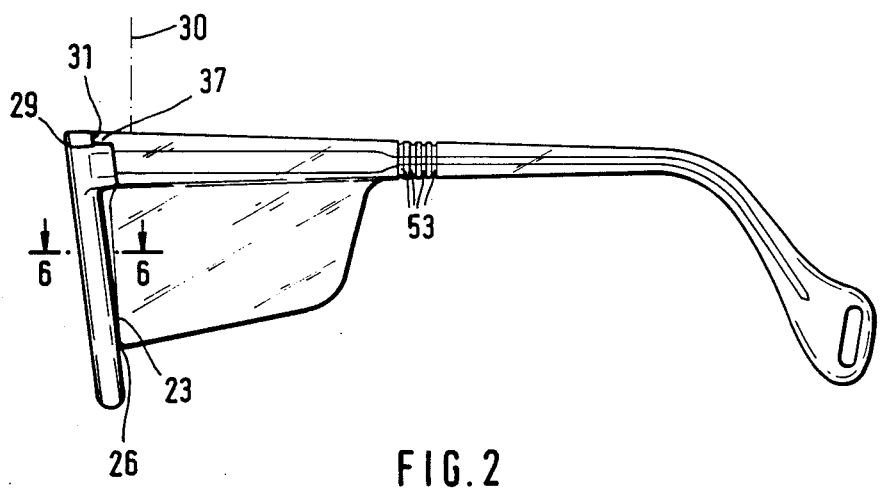

A protective pair of spectacles 11 has a frame 12 of plastic, in which no lenses are yet inserted. A right-hand earpiece 13 carries a protective shield 14. In a similar manner, a left-hand earpiece 16 is provided with a protective shield 17. As shown by FIGS. 1 and 2, the appearance of the protective spectacles 11—apart from the protective shields 14, 17—is as esthetic as is customary for other spectacles. From this partial aspect, there is nothing against the protective spectacles 11. Obviously the protective spectacles 11 can also be worn and stored as is usual for other spectacles.

Figure 4:
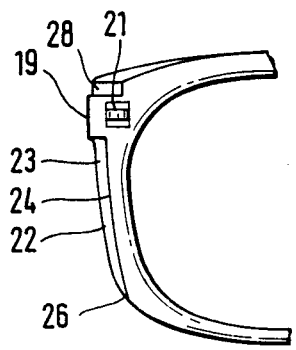

Since the spectacles are symmetrical with respect to the midplane, the same reference numbers will be used below for the left-hand and right-hand parts. A jaw 19 starts from the side profile section 18 of the frame 12 at the tops and goes outwards and rearwards (FIG. 4). A hinge half 21 is sunk into this by its foot from the rear. Below the jaw 19 there begins a step-shaped recess 22, which has a front surface 3 and a side surface 24, the front surface 23 and the rear surface 24 being about perpendicular to each other. These are also substantially flat per se. As particularly shown in FIG. 4, the recess 22 is curved slightly downwards and inwards. In the side view of FIG. 2, the recess is however substantially liner, as seen from the course of the front surface 23. As shown by FIGS. 2 and 4, the end 26 of the recess 22 lies far below and only just above the cheek section 27 of the frame 12

A recess 28, shaped as a circular recess, is formed in the material of the frame above the jaw 19, and its generating circle has its midpoint in the pivot axis of the hinge half 21. The floor 29 of the recess 28 is perpendicular to this axis 30 and equals a sector of a circle. perpendicular to this is the sidewall 31, which runs along a sector of a circle. The parts 22 and 28 are one half of an overlapping profile.

Figure 3:
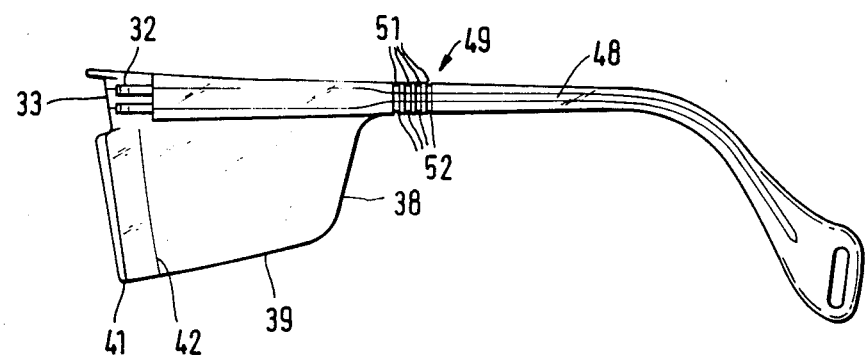
Figure 7:
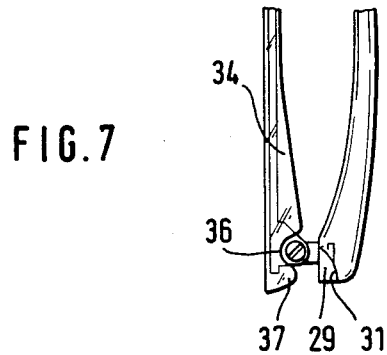

The earpieces 13, 16 possess a hinge half 32, which engages with its two eyelets about the one eyelet of the hinge half 21. The foot of the hinge half 32 is sunk into the plastic material of the earpiece. According to FIG. 3, an earpiece end face 33 is provided to the left of the hinge half 32, and adjoins with it full surface the rear side of the jaw 19, and according to the accuracy of manufacture is gastight to seal against coarse dusts. A thickening 34 which rises gently rearward is provided on the inner side of the earpiece 13, 16, and according to FIG. 7 rises as far as the hinge half 21 is high and begins before the end of the protective shield 17. The thickening 34 then swings away in an approximately semicircular curve 36, so that the head of the hinge screw can be reached with a screwdriver or the like.

A small plate 37 is provided above and in front of the earpiece end face 33; it has a thickness in the millimeter range, and in the opened state of the earpiece 13, 16 can be pivoted into the circular sector shaped recess 28 and fits into this. As can be seen from FIG. 7, the contour of the small plate 37 is round, so that the protective spectacles can be stowed away without damage to pockets or the like.

Figure 5:
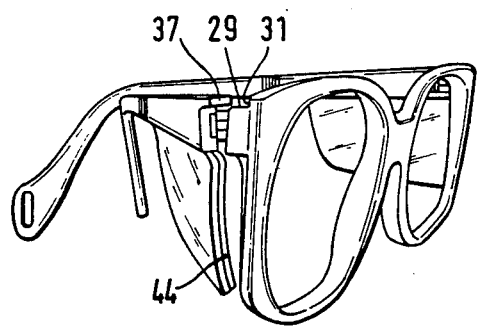
Figure 6:
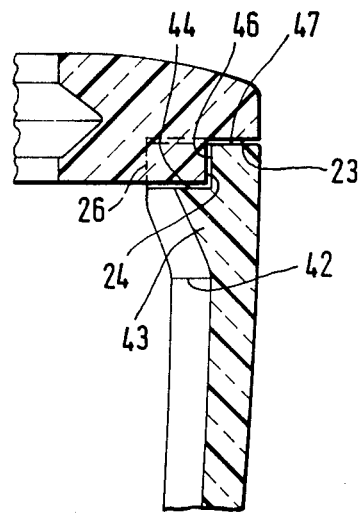

The underside of the earpiece 13, 16 merges integrally into the associated transparent protective shield 17, which, when the protective spectacles 11 are put on, covers the region between the side profile section 18 and the wearer's cheekbone. At about ⅓ the length of the earpiece 13, 16, a bow-like curvature 38 begins, from which the lower edge 39 runs forwards and downwards. In front view, the protective shield 14, 17 is curved, corresponding to the course of the recess 22, as particularly seen in FIG. 4. This curvature can also be seen in FIGS. 5 and 6. The forwardmost, lowermost point 41, in the use position, meets the end 26 of the recess 22. A thickening 43, about triangular in cross section, is provided on the inner side of the protective shield 14, 17 from the line 42, and falls away perpendicularly at an end face 44 and in the position of use abuts the opposite region of the side profile section 18.

The surface 46, which extends forward and projects over the end face 44, is complementary to, and abuts, the side face 24. The forward end face 47 abuts the forward face 23 and it complementary to this. As is particularly clearly shown in FIG. 6, a gap which occurs in all cases has an approximate Z shape. This means an extraordinary degree of sealing in a small space, without loss of esthetic criteria and without excessive demands as regards production. The end face 44, the surface 46 and the end face 47 represent the second half of the overlapping profile.

Such an overlapping profile becomes gastight when its walls are covered with extremely soft silicone rubber or the like.

A metallic wire 48 is provided in the middle of the earpiece material.

A zone 49 provided directly after the curvature 38; it has four horizontal notches 51, 52 on the upper side and the underside of the earpiece 13, 16. The earpieces 13, 16 can be bent in this zone 49 to adjust the inclination, without altering the proportions in the overlapping profile. The notches 51, 52 are aligned in height, i.e., they are not mutually offset.

The side surfaces of the earpieces 13, 16 merge in the zone 49 into respectively four perpendicular notches 53, which in turn are aligned with the notches 51, 52. These notches 53 make it possible to bend inwards or outwards the part of the earpiece 13, 16 located, according to FIG. 3, to the right of the zone 49, instead of changing the curvature of the earpiece by working in the region of the hinges. The earpiece curvature can thus be adjusted, again without altering the relationships in the region of the overlapping profile.

I claim:

1. In a protective spectacles comprising a frame for lenses, having side profile sections, first hinge halves temporally fitted on the frame, earpieces having in their forward end region second hinge halves, which together with the first hinge halves form hinge zones for the earpieces, the improvement wherein
   (a) protective shields extend out rearward from the side profile section of the frame in the opened state of the earpieces,
   (b) the protective shields are firmly connected at their upper edge regions to an associated earpiece,
   (c) a predetermined bending zone is located on each earpiece following the protective shield,
   (d) the bending zone is of a design adapted to alter the inclination of each earpiece upwards and downwards to a desired inclination relative to the frame and hold each earpiece in the desired inclination,
   (e) the protective shields have forward edge profiles,
   (f) the side profile sections of the frame have regions opposite the forward edge profiles of the protective shields in the opened state of the earpieces,
   (g) the forward edge profiles of the protective shields and the opposite regions of the side profile sections of the frame are arranged and adapted to form sealed over-lapping profiles in the opened state of the earpieces,
   (h) the protective shields are integral with the earpieces,
   (i) the frame has an upper back that provides a gripping lateral jaw and anchors each first hinge half, and
   (j) each earpiece has a small plate above and to the side of the hinge pivot axis that engages in a complementary recess on the frame above the lateral jaw.

2. Protective spectacles according to claim 1, wherein the protective shields are of translucent material.

3. Protective spectacles according to claim 1, wherein the protective shields are of transparent material.

4. Protective spectacles according to claim 1, wherein the overlapping profiles are substantially linear in side view of the spectacles, and in front view follow a radius which is bent downwards and inwards from the hinge zones.

* * * * *